United States Patent [19]
Gollihar et al.

[11] Patent Number: 5,825,958
[45] Date of Patent: Oct. 20, 1998

[54] FIBER OPTIC DELIVERY SYSTEM FOR INFRARED LASERS

[75] Inventors: William A. Gollihar, Perris; Larry G. DeShazer, Newport Beach; Scott Bradley, Laguna Niguel, all of Calif.

[73] Assignee: Pharos Optics, Inc., Tustin, Calif.

[21] Appl. No.: 729,425

[22] Filed: Oct. 11, 1996

Related U.S. Application Data

[60] Provisional application No. 60/010,569, Jan. 25, 1996.

[51] Int. Cl.[6] .................................................. G02B 6/02
[52] U.S. Cl. ........................... 385/125; 385/102; 385/115; 385/117; 385/147; 604/14; 606/15; 606/16; 372/6
[58] Field of Search .................................. 385/125–127, 385/128, 139, 147, 60, 31, 102, 115, 117, 124, 123; 604/4, 14, 15, 16, 17; 372/6; 606/15, 14, 16

[56] References Cited

U.S. PATENT DOCUMENTS

| | | | |
|---|---|---|---|
| Re. 32,436 | 6/1987 | Hartig | 350/96.23 |
| 3,382,343 | 5/1968 | Muncheryan | 219/121 |
| 3,383,441 | 5/1968 | Norrhede et al. | 264/51 |
| 3,383,491 | 5/1968 | Muncheryan | 219/121 |
| 3,622,743 | 11/1971 | Muncheryan | 128/303.1 |
| 3,821,510 | 6/1974 | Muncheryan | 128/303.1 X |
| 4,169,657 | 10/1979 | Bedard | 350/96.23 |
| 4,407,561 | 10/1983 | Mysocki | 350/96.3 |
| 4,606,608 | 8/1986 | Wysocki | 350/96.33 |
| 4,781,432 | 11/1988 | Zongor et al. | 350/96.23 |
| 5,030,217 | 7/1991 | Harrington | 606/14 |
| 5,108,703 | 4/1992 | Pfost et al. | 422/65 |
| 5,168,538 | 12/1992 | Gillespie | 385/123 |
| 5,257,935 | 11/1993 | Vassiliadis et al. | 433/215 |
| 5,275,564 | 1/1994 | Vassiliadis et al. | 433/226 |
| 5,304,172 | 4/1994 | Manoukian et al. | 606/15 |
| 5,318,562 | 6/1994 | Levy et al. | 606/16 |
| 5,342,198 | 8/1994 | Vassiliadis et al. | 433/215 |
| 5,349,590 | 9/1994 | Amirkhanian | 372/6 |
| 5,401,171 | 3/1995 | Paghdiwala | 433/215 |
| 5,651,783 | 7/1997 | Reynard | 606/4 |
| 5,664,036 | 9/1997 | Islam | 385/31 |

FOREIGN PATENT DOCUMENTS

| | | |
|---|---|---|
| 0 109 695 | 5/1984 | European Pat. Off. |
| 64-4713 | 1/1989 | Japan |
| WO9707928 | 6/1997 | WIPO ............. B23K 26/14 |

OTHER PUBLICATIONS

Ioana M. Rizolu et al., "New Laser—Matter Interaction Concept to Enhance Hard Tissue Cutting Efficiency," *Proceedings of Laser–Tissue Interaction V*, Progress in Biomedical Optics, SPIE vol. 2134A, pp. 307–317, Jan. 1994, Los Angeles, CA.

Gregory B. Altshuler, et al., "Physical aspects of cavity formation of Er–laser radiation", St. Petersburg Institute of Fine Mechanics & Optics, Department of Quantam Electronics & Biomedical Optics, Russia, SPIE vol. 2394, pp. 211–222, 1995.

*Primary Examiner*—Phan T. H. Palmer
*Attorney, Agent, or Firm*—Koppel & Jacobs

[57] ABSTRACT

A hand held laser device is disclosed including a handpiece coupled to a source of laser energy by an optical fiber cable. A bias tensile stress is exerted on the fiber when the fiber and outer sheathing or tube are straight in-line. The bias tensile stress reduces compressional stress on the fiber when the fiber cable is bent. Moreover, the fiber is coupled to a disposable fiber in the handpiece to output light from the laser to a target area. The two fibers are precisely spaced close to one another to permit substantial lossless transmission of light without lenses or other focusing optics. Further, precision bearing devices are provided at opposite ends of the fiber cable in order to reduce torque on the fiber.

45 Claims, 12 Drawing Sheets

FIBER OPTIC DELIVERY SYSTEM FOR INFRARED LASERS

This application claims the benefit of provisional application Ser. No. 60/010,569 filed Jan. 25, 1996.

BACKGROUND OF THE INVENTION

1. Field of the Invention

The present invention relates to a laser device. In particular, the present invention is directed to a fiber-optic delivery system for medical applications.

2. Description of the Prior Art

Lasers, especially those emitting infrared light, have been used to treat a wide range of medical disorders. In such applications, however, it is frequently difficult to direct the laser light to a target area for treatment. Thus, hand held laser devices have been proposed whereby the user can easily point a handpiece emitting laser light to the target area.

Conventional hand held laser devices include a stationary or fixed laser coupled to the handpiece by an optical fiber, thereby constituting a fiber-optic delivery system. Typically, the optical fiber is inserted into a crush-resistant protecting tube of high density material, such as the plastic polyetheretherketone (PEEK). The fiber is next fixed to the tube by ferrules, small cylindrical holders usually made of aluminum, when the protecting tube, fiber, and ferrules are fixed in a straight line. Accordingly, no tensile stress is applied to the fiber while it is fixed to the tube.

Light generated by the laser is transmitted to the handpiece. The user can then expose the target area with a laser beam by appropriate manipulation of the handpiece. Frequently, however, the target area can be difficult to reach, particularly in dental applications where it is necessary to position the handpiece in a patient's mouth. Thus, a significant amount of strain can be induced in the fiber by excessive manipulation of the handpiece. While standard silica glass fibers are relatively strong and can withstand such strain, others are not. In particular, those fibers having a high transmissivity at wavelengths suited for medical applications, e.g., in the infrared, are brittle and tend to break when strained. Accordingly, even though the optical properties of these fibers are ideally suited for medical and therapeutic purposes, they have not been widely adopted in medical laser systems.

SUMMARY OF THE INVENTION

In accordance with the present invention, an optical device is provided comprising a waveguide and a sheathing substantially surrounding the waveguide. The sheathing exerts a tensile strain on the waveguide when the sheathing and waveguide are in a straight line configuration. Accordingly, when the sheathing and waveguide are bent, any resulting compressional strains are offset by the initial tensile strain set in the waveguide.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Reference will now be made in detail to exemplary embodiments of the invention, examples of which are illustrated in the accompanying drawings. Wherever possible, the same reference numbers will be used throughout the drawings to refer to the same or like parts.

Figure 1A:
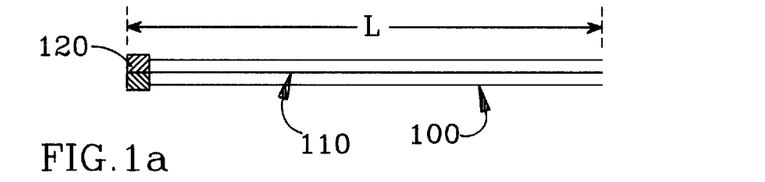
FIGS. 1(a)–1(c) illustrate a fiber cable.
Figure 1B:
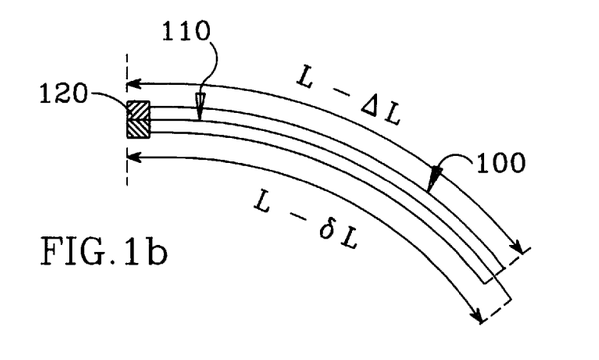
Figure 1C:
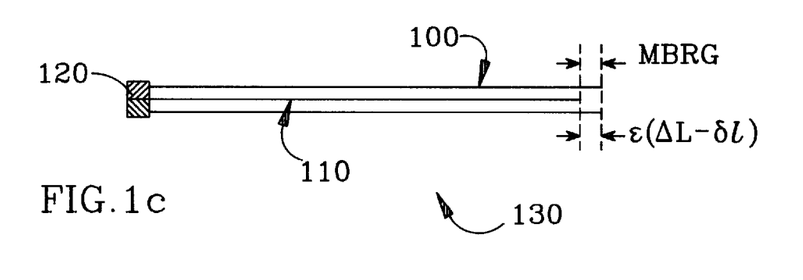

The inventors have discovered that fragile non-silica fibers, when inserted through a protective tubing or sheath, buckle and break under a compressional stress when the tubing and fiber are excessively bent or flexed. This unexpected compressional stress was discovered to be due to the difference in compliancies between the fiber and tube. That is, as shown in FIGS. 1(a) and 1(b), when a tube 100 of length L is bent in a curve, its length contracts by a certain amount $\Delta L$, primarily due to a change in tubular cross-section from circular to elliptical. Accordingly, the length of the curved tube is L-$\Delta L$ when bent. Fiber 110 is bent inside tube 100 at the same curvature, but has its length reduced to L-$\delta\iota$. It was found that the change in fiber length $\delta\iota$ is much smaller (~0.1 mm) than the change in tube length $\Delta L$ (~5 mm), for length L of 1.5 meter and radius of curvature of 20 cm, where fiber 110 is made of germanium oxide glass fiber and tubing 100 is made of polyetheretherketone (PEEK) tubing 100. Moreover, in this case, tubing 100 preferably has an outer diameter of 1.8 mm and a 0.5–1.2 mm inner diameter, but these values depend on fiber diameter, which may range from 0.2 to 1.1 mm. Other fiber/tube combinations, with differing compositions and diameters of fiber and tubes, demonstrate the same effect, but with slightly different values of $\Delta L$ and $\delta\iota$.

As further shown in FIG. 1(b), with fiber 110 fixed to tube 100 at one end by a ferrule 120, the fiber 110 protrudes farther out of the tube when the fiber cable is bent, than when it is straight. Thus, under bending, tube 100 contracts, causing fiber 110 to compress, buckle and break because it is restricted by the inner wall of the tube.

In order to relieve the compressional stress experienced by fiber 110 in accordance with the present invention, a preset bias tensile strain is imported to fiber 110 when it is cabled in tube 100. The appropriate tensile bias is determined by measuring both the "minimum bend radius" (MBR), i.e., the smallest radius of curvature that the fiber can be bent without fracture of unpackaged (naked) fiber, and the relative length contraction $\Delta L$-$\delta\iota$ at the desired length L and MBR. The fiber is preferably marked at a length L-$\epsilon(\Delta L$-$\delta\iota)$ in the straight position, where $\epsilon$ is a fractional number depending on the fiber/tube composition. For monocrystalline sapphire fiber and PEEK tubing, $\epsilon$ is about 0.7–0.8, while for germanium oxide (GeO) glass fiber and the same tubing, $\epsilon$ is about 0.5–0.6. The variation in $\epsilon$ is due to the various fiber diameters chosen. Generally, an $\epsilon$ value of 1 is not chosen because it would determine an excessive tensile strain bias for fiber 110. The MBR is preferably 5 cm for fibers carrying near infrared wavelengths (913 nm–2.2 $\mu$m) and 20 cm for fibers carrying mid infrared wavelengths (2.2–19 $\mu$m) and the length of the fiber 110 can be up to 10 meters.

The loose fiber end is then permanently fixed to ferrule 120 at the marked length (for example, for GeO glass fiber, that length would be about 1.74 mm shorter than 1.5 meters, the tube length). After polishing the fiber 110, to shorten its length by the amount of the Minimum Bend Radius Gap (MBRG=[$\epsilon(\Delta L$-$\delta\iota)$]), tube 100 is fixed to ferrule 120. Fiber 110 and tube 100 are then bent to 40%–60% of the MBR. A second ferrule (see SMA connector 370 in FIG. 3, to be discussed below) is then attached. Fiber 110 and tube 100 are next straightened so that the fiber is stretched, thereby giving the bias tensile strain. Preferably, for relatively large tube and fiber diameters, fiber 110 and tube 100 should be bent to 40% of the MBR, but for smaller tubes and fibers, the fiber and tube should be bent to 60% MBR.

As a result, when fiber cable 130 of the present invention is bent, the compressional strain experienced by the fiber is reduced by the tensile bias strain. Fiber 110 and tube 100 can thus bend and flex essentially as one complete unit, i.e., with negligible relative movement. Moreover, at some radius of curvature, the strain becomes zero. Therefore, in accordance with the present invention, fragile fibers (i.e., fibers that readily break under stress), such as monocrystalline sapphire fibers, polycrystalline KRS5 (thallium halide) fibers, hollow waveguide glass fibers, germanium oxide glass fibers, and fluoride glass fibers including tellurium halide (TeX) fibers, can be packaged reliably into cables. Preferably, however, fiber 110 and tube 100 should be carefully fixed to ferrule 120 to avoid further straining the fiber.

Preferably, bending stress on the fiber is 2% for fibers carrying near infrared wavelengths and 10% for fibers carrying mid infrared wavelengths.

Figure 2:
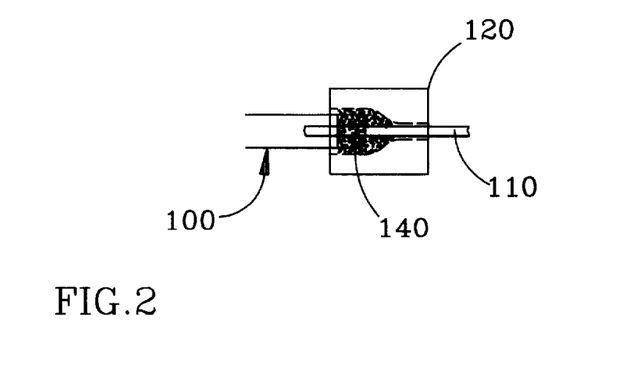
FIG. 2 is a cross-sectional view of a portion of ferrule 120 shown in FIG. 1(c)

FIG. 2 schematically presents how fiber 110 and tube 100 are individually fixed to ferrule 120. In particular, it is preferred that tubing 100 and fiber 110 be fixed to an inside portion of ferrule 120 by epoxy 140 in order to achieve appropriate tensile strain bias.

Figure 4:
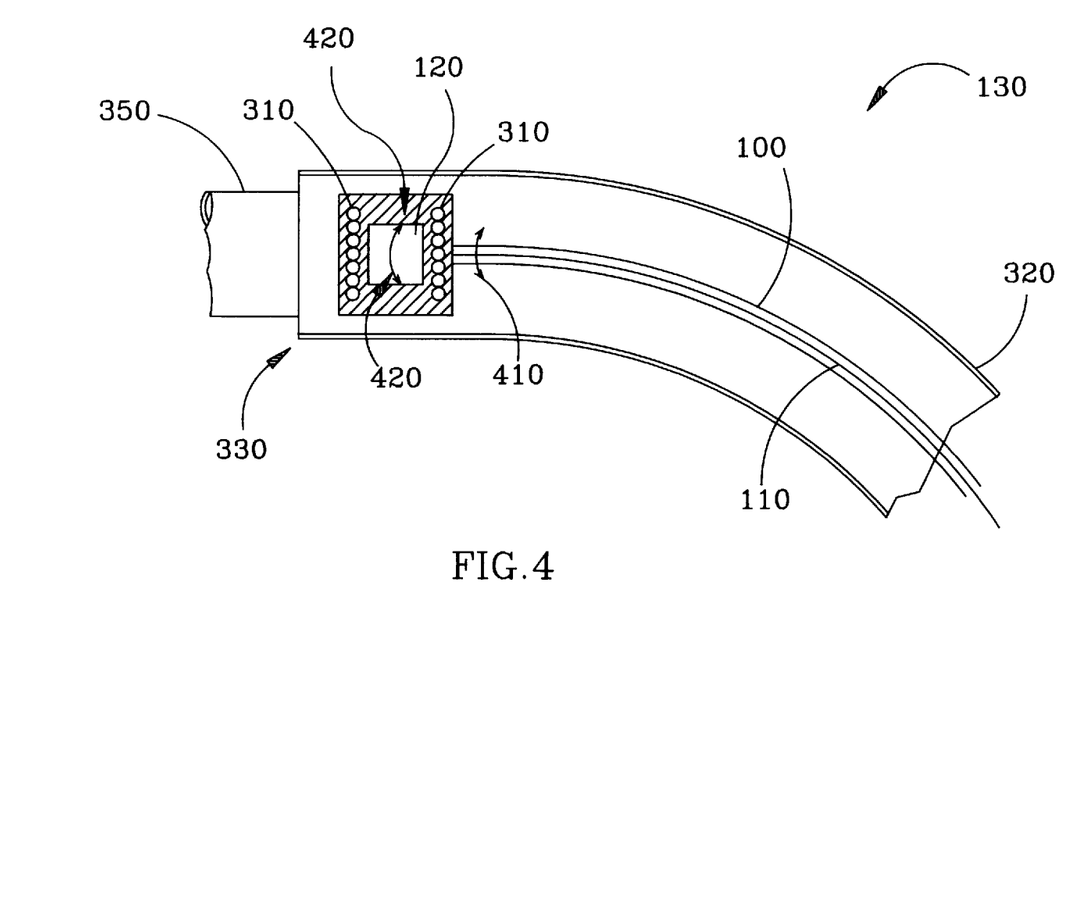
FIG. 4 is a detailed longitudinal-sectional view of a portion of the fiber cable shown in FIG. 1(c)

Preferably, PEEK tubing is used because it provides crush resistance to pressures up to 3,000 pounds per square inch (200 atmospheres). Further, additional or outer tubing 320 (see FIG. 4) can surround the PEEK tubing to prevent bending of cable 130 beyond radii of curvature smaller than the MBR. This outside tube may be fluorinated ethylene-propylene (Teflon®FEP) plastic tubing.

Figure 3:
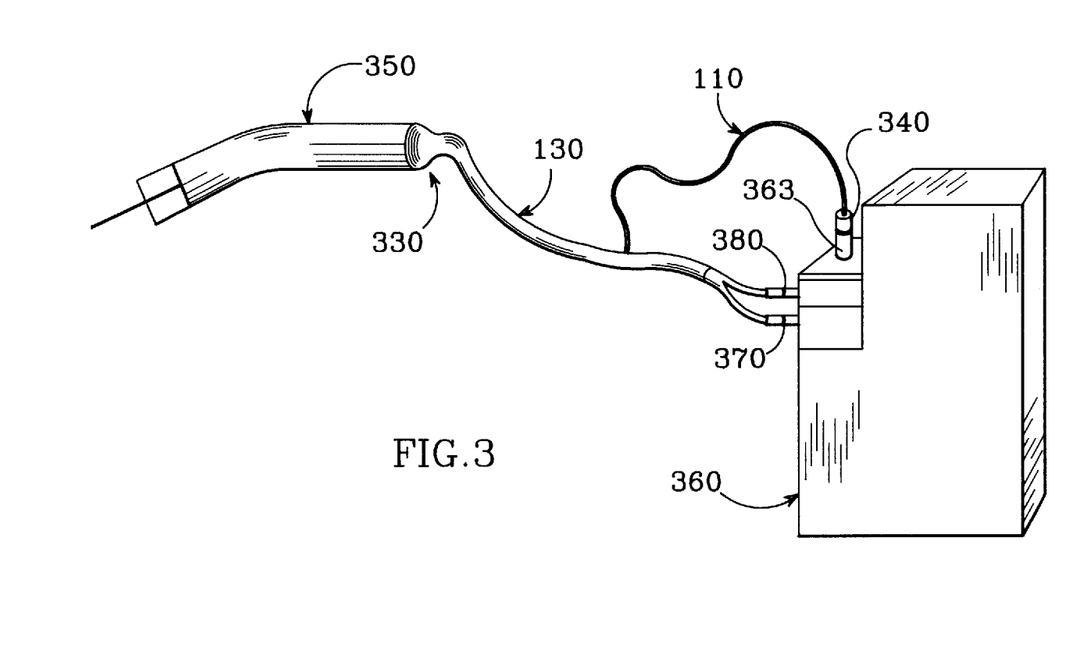
FIG. 3 illustrates a fiber-optic delivery system in accordance with the present invention.

FIG. 3 illustrates a fiber optic delivery system in accordance with the present invention including a fiber cable 130 coupled to a handpiece 350 at port 330 and to laser/water and air supply 360 at ports 340, 370 and 380. Fiber 110 is coupled to the laser output of the supply 360 by connection of ports 340 and 363, preferably using Sub-Miniature type-A (SMA) connectors. Further, fiber cable 130 also carries air and/or water to handpiece 350 from air supply output 370 and water supply output 380. Air and water supply to handpiece 350 will be described in greater detail below.

Figure 5:
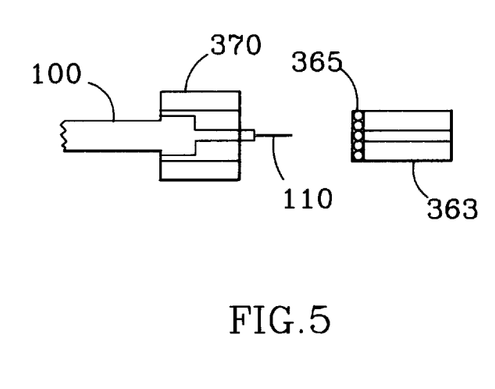
FIG. 5 illustrates an SMA connection used in accordance with the present invention.

Returning to FIG. 3, fiber 110 is protected from torque stress and excessive rotation by bearings located at ports 330 and 340 coupled to handpiece 350 and laser/air and water supply 360, respectively. As further shown in FIG. 4, bearings, preferably precision ball bearing members 310, are provided in cable 130 and in 310 of handpiece 350. As indicated by arrows 410 and 420, when tube 100 and fiber 110 rotate, ferrule 120 can also rotate, both with respect to outer tubing 320 of cable 130 and with respect to handpiece 350. Moreover, as shown in FIG. 5, an additional precision bearing member 365 is provided on SMA port 363 at port 340. Thus, fiber 110 can freely rotate relative to outer tubing 320 and coupling ports without being subject to significant torque.

By using such a precision bearing coupling arrangement, fiber 110 will not be stressed when rotated or twisted by the user in accessing difficult targets, when fiber cable 130 is coiled for storage, or when the delivery system is placed in an autoclave for sterilization.

Preferably, in accordance with the present invention, two fibers are used to couple laser light to the site of treatment. The first fiber, fiber 110, as described above, has one end coupled to a laser source in supply 360 and the other end coupled to the handpiece. A second fiber, however, is provided in the handpiece with a first end coupled to receive the laser light from the first fiber 110 and a second end from which a laser beam is emitted. In order to simplify construction of the handpiece and the end-to-end coupling of the first and second fibers, the first and second fibers are preferably coupled serially without lenses or other focusing optics, such as curved surfaces and mirrors. Accordingly, the integrity of the serial coupling of the first and second fibers can be made insensitive to misalignment during use, shipping of the product, and mishandling of the handpiece.

The optical coupling of the first and second fibers will now be described with reference to FIG. 6. The coupling in accordance with present invention is preferably accomplished by using close tolerances of fiber alignment, and use of a near-contact approach to deliver the laser light from the first fiber, fiber 110, to the second fiber, fiber 610, and onto the target.

Figure 6:
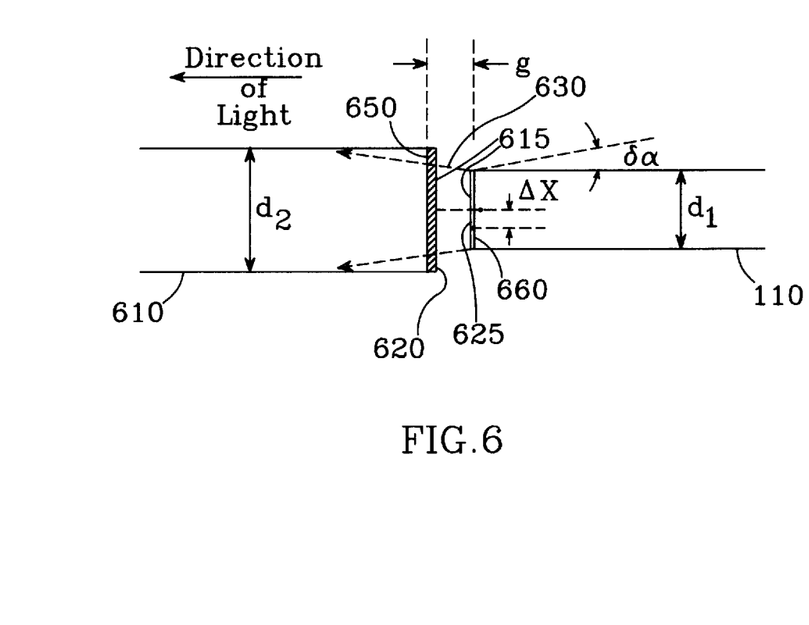
FIG. 6 illustrates an optical coupling between fibers 110 and 610.

As shown in FIG. 6, fibers 110 and 610 are substantially accurately aligned axially (face centers 615 are preferably offset by a $\Delta x$ value not more than ±12 microns per fiber) and concentrically to the next fiber to achieve optimum optical transmission. It was discovered that, if the spacing or gap g between the two fiber faces is made small enough (25 to 100 microns, depending on fiber diameter), only the centers of the two fiber faces need to be substantially coaligned, and the angular alignment of the fibers' axes, $\delta\alpha$, can be neglected. The optimal gap distance was determined experimentally but is believed to be a function of the laser beam divergence, the numerical aperture (NA) of the smaller fiber (preferably approximately 0.2), the diameters of the two fibers $d_1$ and $d_2$, and the center misalignment $\Delta x$ (see FIG. 6). The efficiency with which laser light is transmitted between fibers 110 and 610 is dependent on the accuracy with which the fiber axes are coaligned. The efficiency decreases by about 12% for a 25 micron misalignment. In order to achieve the proper fiber connection, fibers 110 and 610 are joined together with an air gap between the fibers' ends. This coupling is effected as shown in FIG. 7(d) by using a hollow metal sleeve, called a coupler 7, into which ferrules 4 and 120 are inserted. The coupler 7 has a step in the internal diameter which seats a stainless-steel flat donut spacer 17a, having a thickness within a range of 25–100 μm. The surfaces of the ferrules 4 and 120 which face each other are polished flat and placed next to the spacer 17a, accurately setting the air gap 17b to the thickness of the spacer 17a.

Preferably, in order to improve transmission of laser light from fiber 110 to fiber 610, the diameter of fiber 110 is made smaller than that of fiber 610. For example, the diameter of fiber 110 is preferably between 400 μm to 600 μm, and the diameter of fiber 610 is between 600 μm and 1mm. Fiber 610 receives the laser light without the use of optics and allows beam 630 emanating from fiber 110 to diverge without causing laser damage to the delivery system components. Moreover, antireflection dielectric coatings 650 and 660 are preferably provided on faces 620 and 625, respectively, to reduce unwanted reflection losses or heating caused by fiber surface loses.

FIGS. 7(a)–(c), 8(a)–(c) and 9(a)–(c) illustrate in detail three implementations of the novel coupling scheme in the handpiece.

Figure 7A:
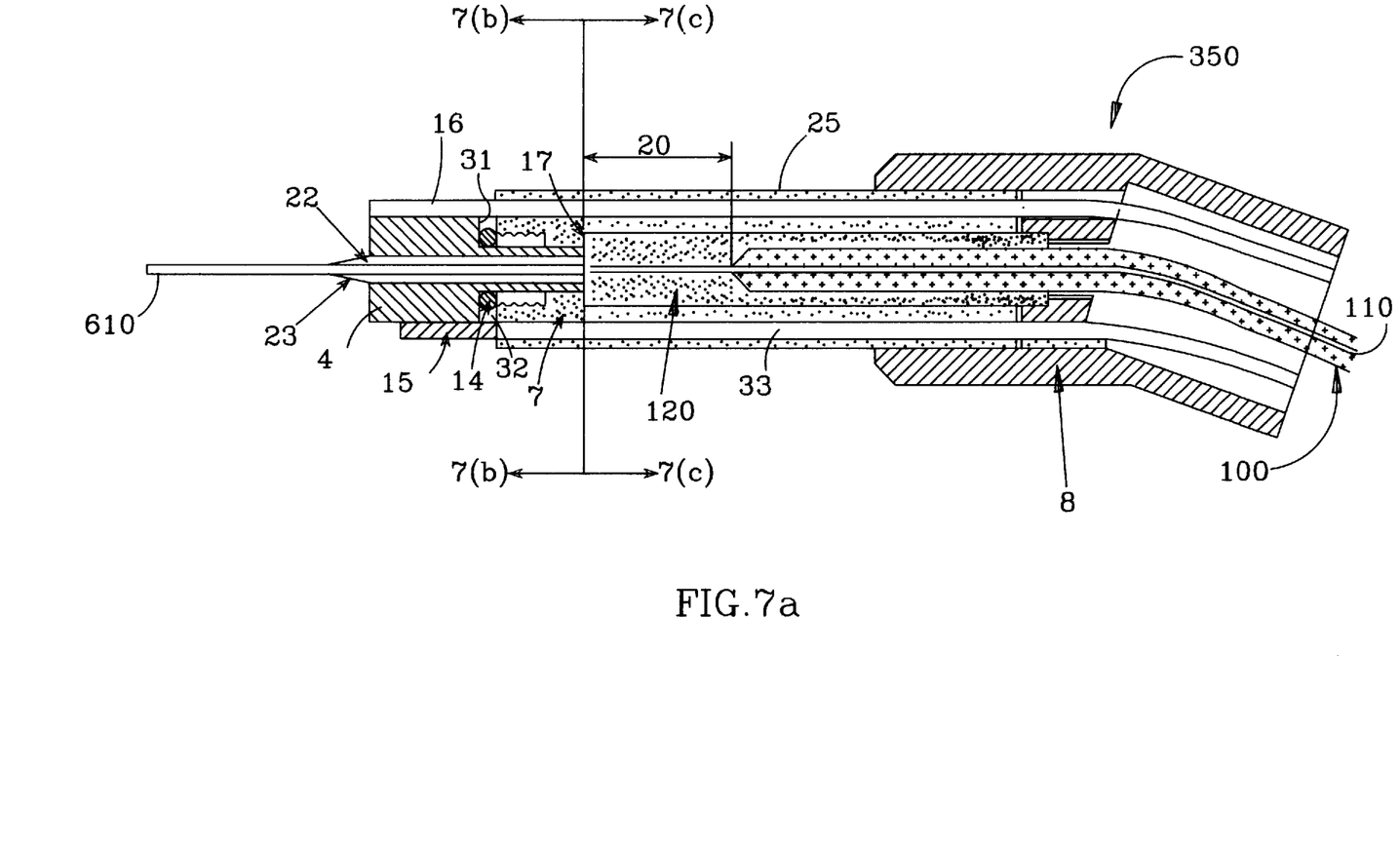
FIG. 7(a) illustrates a detailed longitudinal-sectional view of a handpiece in accordance with the present invention.

As seen in FIG. 7(a), fiber 110 and tube 100 are fitted within ferrule 120. Preferably, fiber 110 extends beyond tube 100 by a length 20 of approximately 4 to 7 times the diameter of fiber 110 in order to insure that fiber 110 is properly secured to ferrule 120, which is inserted into one end of fiber-to-fiber coupler 7. The other end of fiber-to-fiber coupler 7 receives a ferrule 4 having fiber 610 fixed therein. Preferably, ferrule 4 includes a sleeve 22 formed of a laser-tolerant material (Pyrex, silica or sapphire depending on the wavelength being used) surrounding fiber 610. Dielectric sleeve 22 permits fiber 610 to have a smaller diameter because any energy that is not transmitted by fiber 610 (due to scattering or refraction) is absorbed by sleeve 22. Since sleeve 22 is more laser-tolerant than the ferrule metal, damage to the ferrule 4 is avoided, and the fiber 610 is protected from damage. Moreover, sleeve 22 has a tapered portion 23, as further shown in FIG. 7(a), in order to allow laser energy to leak out in a moderate fashion.

As further shown in FIG. 7(a), an O-ring 14 is fitted around a reduced diameter portion of ferrule 4 impose a compression gap 32 between face 31 of ferrule 4 and fiber-to-fiber coupler 7. Moreover, ferrule 4 fits snugly into fiber-to-fiber coupler 7 so that an appropriate, small gap 17 is maintained between fiber 110 and fiber 610, so that substantially transmission of light can occur between these two fibers.

An acoustic sensor 15 is preferably coupled to ferrule 4 to convert sonic energy emanating from the target area into electrical signals. Since this sonic energy is an indication of the amount of material ablated from the target, these electrical signals can be used to control the output of the laser source in supply 360. In particular, the electrical signals are preferably conducted by wiring 33 running through handpiece 350 and cable 130 to laser output control circuitry located in the laser/ water and air source 360.

In certain applications it may be necessary to cool the target. Accordingly, a water tube 16 is provided to carry water from laser/water and air source 360 to the forward end of handpiece 350, from which a water stream can be directed onto the target.

Lastly, handpiece 350 preferably includes first and second outer housings 25 and 8 which enclose ferrule 4, wiring 33, fiber-to-fiber coupler 7, and water tube 16.

Figure 7B:
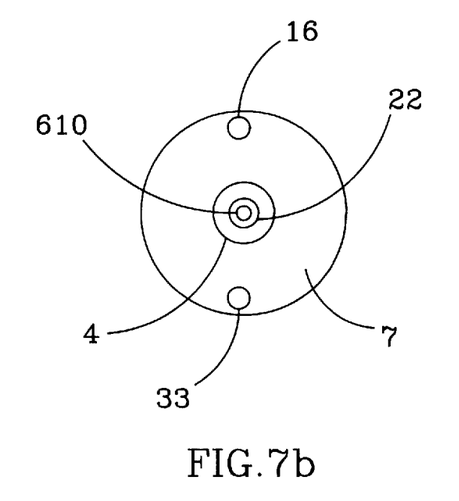
FIGS. 7(b)–7(d) illustrate different cross-sectional views of the handpiece shown in FIG. 7(a)
Figure 7C:
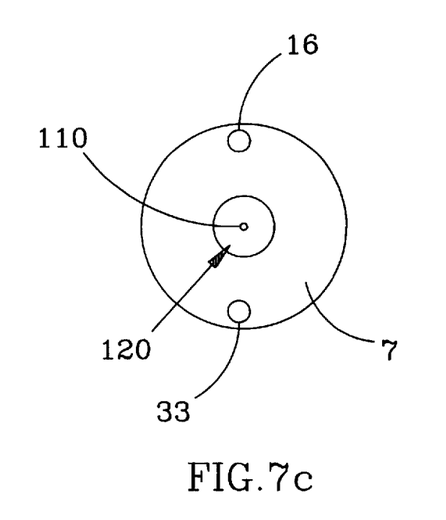
Figure 7D:
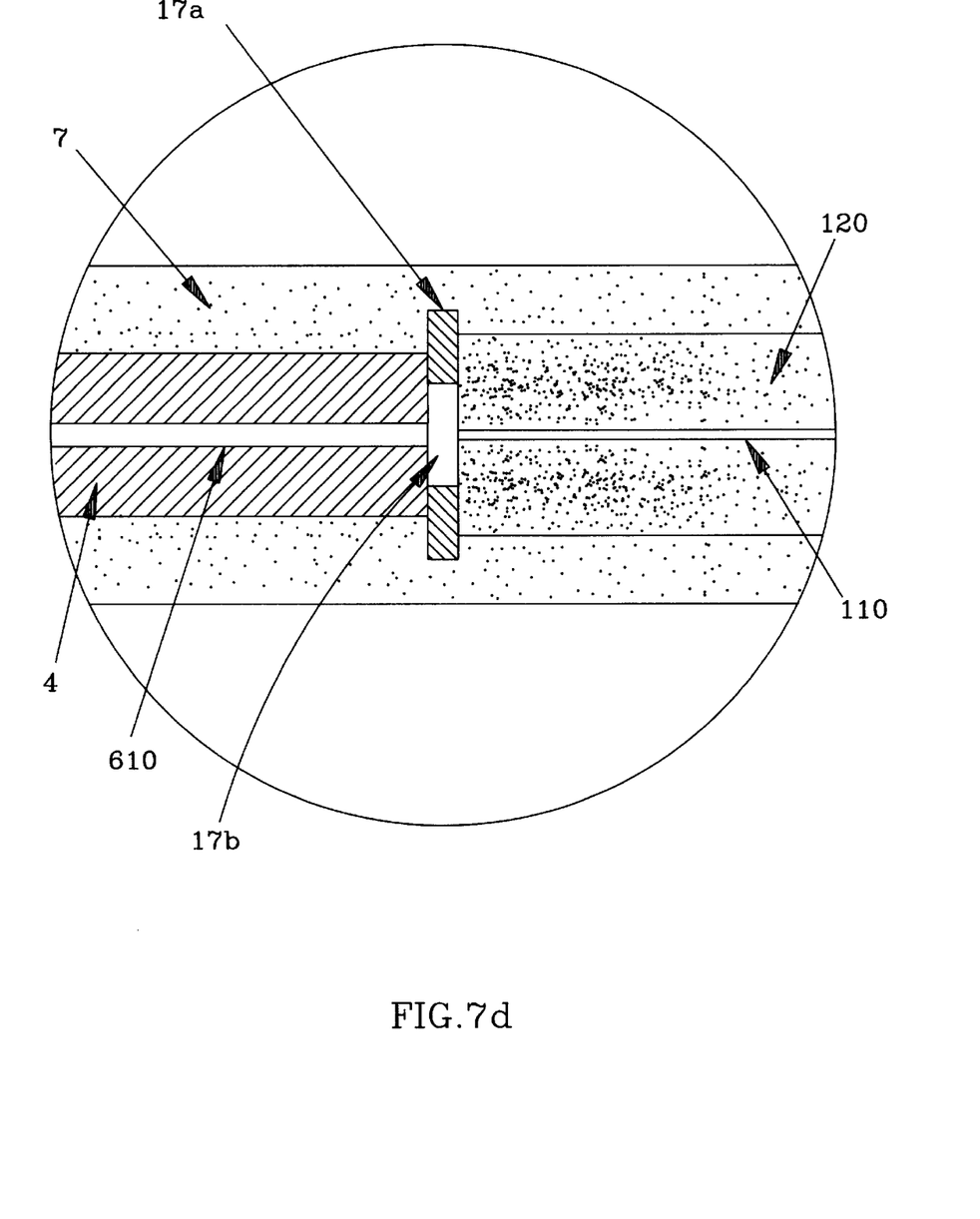

To further illustrate the handpiece construction in accordance with the present invention, FIGS. 7(b) and 7(c) show sectional views of handpiece 350 observed in directions 7(b) and 7(c) indicated in FIG. 7(a).

Figure 8:
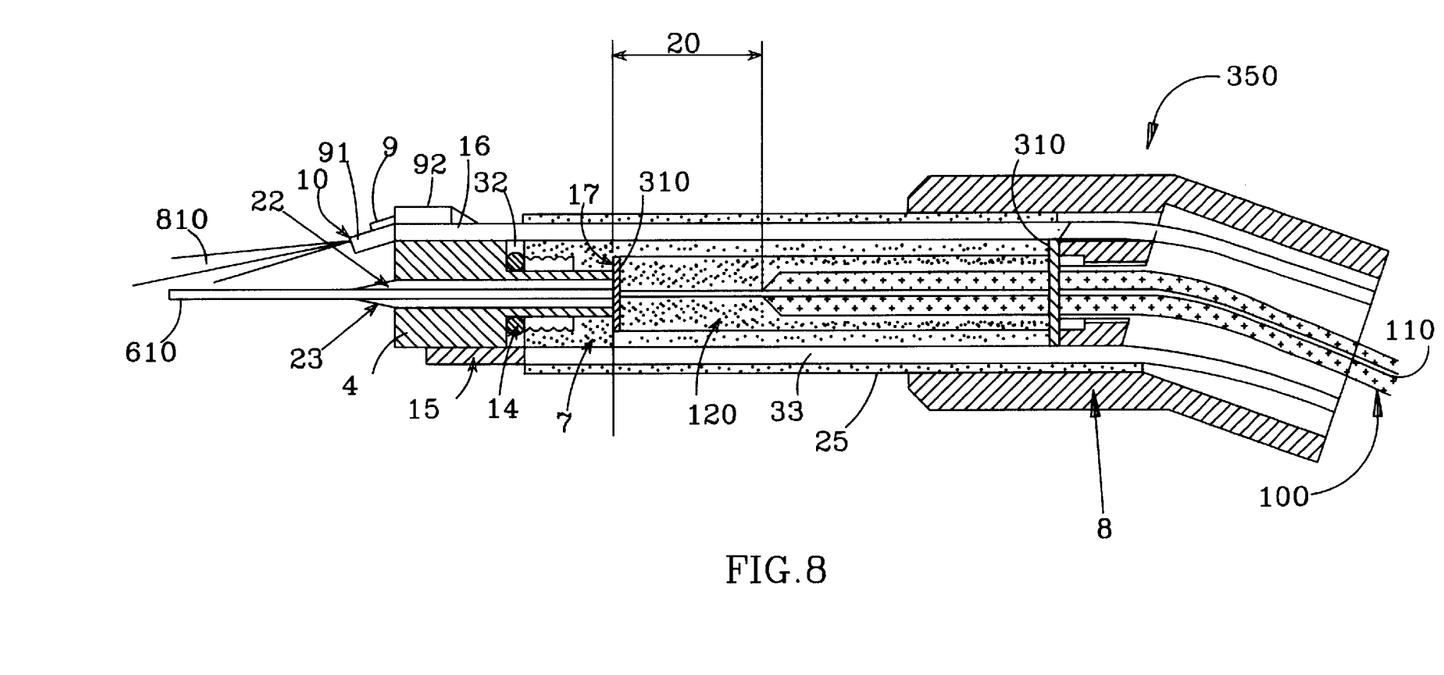
FIG. 8 illustrates a detailed longitudinal-sectional view of a handpiece in accordance with an additional embodiment of the present invention.

A handpiece in accordance with a further embodiment of the present invention is shown in FIG. 8, which is similar to the embodiment shown in FIGS. 7(a)–7(c). The current embodiment, however, includes a regulated diameter nozzle 10 with a taper provided within a housing 9 at the discharge end portion of water tube 16. With this construction, a fine water spray 810 can be generated, which produces a "safe zone" in which material being ablated or removed from the target area can not blow back onto the output face of fiber 610. Accordingly, water spray 810 prevents heating and surface damage to fiber 610.

It is noted that pressured air-water spray is usually used as a coolant in laser cutting systems, but pressured sprays can pose problems in keeping the fiber interfaces free of water in a fiber delivery system. Accordingly, high gas purge pressure would be required to keep the interfaces free of water, in which higher pressures would be needed to overcome the combined pressures of both air and water streams. This invention reduces the pressure required to keep the interfaces free of water. As discussed above, a nozzle 10, whose aperture size is regulated by a tapered pin 91 placed within housing 9 and moved by pin adjustment 92, provides a variable orifice to regulate the water drop size in order to produce the desired water spray. No pressurized air is required by this technique of producing a water spray. An adjustable water flow system is regulated by water pressure to control the drop density for the particular drop size. Such adjustable waterflow and drop size control can also be achieved using a mesh or screen as discussed in greater detail below.

As further shown in FIG. 8, precision bearing devices 310 are provided to reduce torque exerted on fiber 110, as discussed above.

Figure 9A:
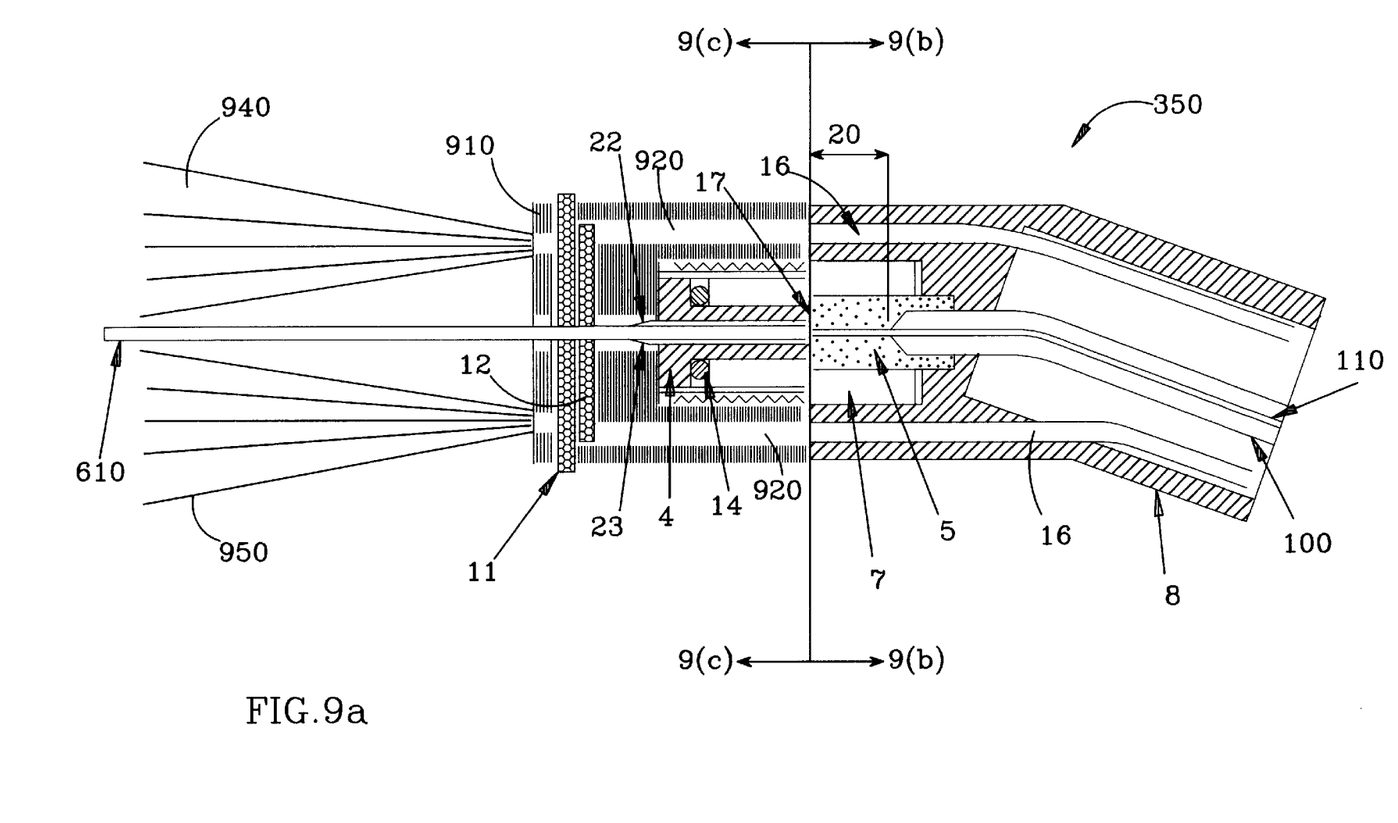
FIG. 9(a) illustrates a detailed longitudinal-sectional view of a handpiece in accordance with a further embodiment of the present invention.

A handpiece in accordance with yet another embodiment of the present invention is illustrated in FIG. 9(a). The current embodiment differs from the embodiment shown in FIG. 8 in the manner in which the water spray is generated. As further shown in FIG. 9(a), ferrule 4 is mounted within a cap 910 having openings 920 bored therein. Openings 920 are preferably aligned with water tubes 16 to supply water through fine screens or meshes 11 and 12 to output water sprays 940 and 950. Preferably, screens 11 and 12 are movable relative to each other in order to control droplet size of water sprays 940 and 950.

Figure 9B:
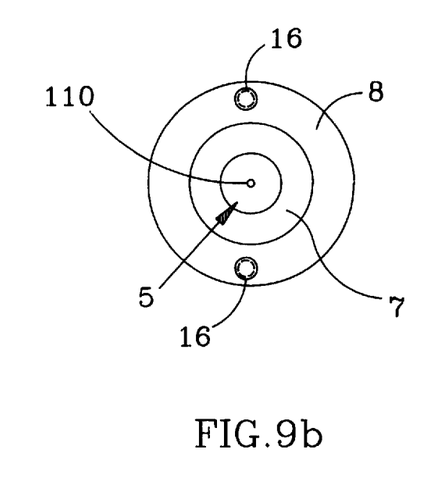
FIGS. 9(b) and 9(c) illustrate different cross-sectional views of the handpiece shown in FIG. 9(a)
Figure 9C:
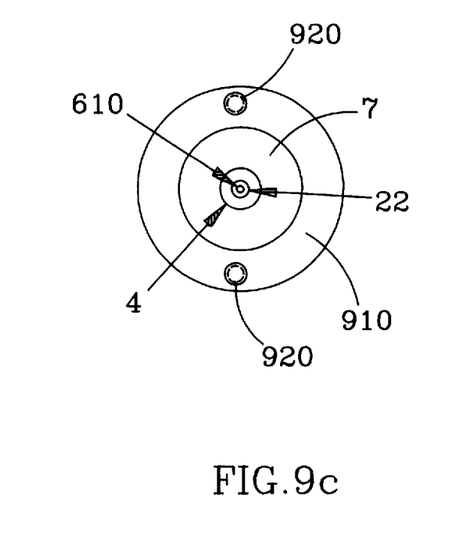

To further illustrate the handpiece in accordance with the present invention, Figs.9(b) and 9(c) show sectional views of handpiece 350 observed in directions 9(b) and 9(c) indicated in FIG. 9(a).

Preferably, handpiece 350 has a length of 12.5 cm and a diameter about ferrule 4 is 8.5 mm. Further, handpiece 350 is preferably bent at an angle of 0–90 degrees for near infrared wavelengths (913 nm–2.2 μm) and 0–45 degrees for mid-infrared wavelengths (2.2–19 μm).

In addition, the above-described fiber optic delivery system can supply 750 mJ per pulse at mid-infrared wavelengths and 2J per pulse at near infrared wavelengths. Preferably, the pulses are supplied at 10–30 Hz with pulse widths of 100 to 240 μs.

Figure 10A:
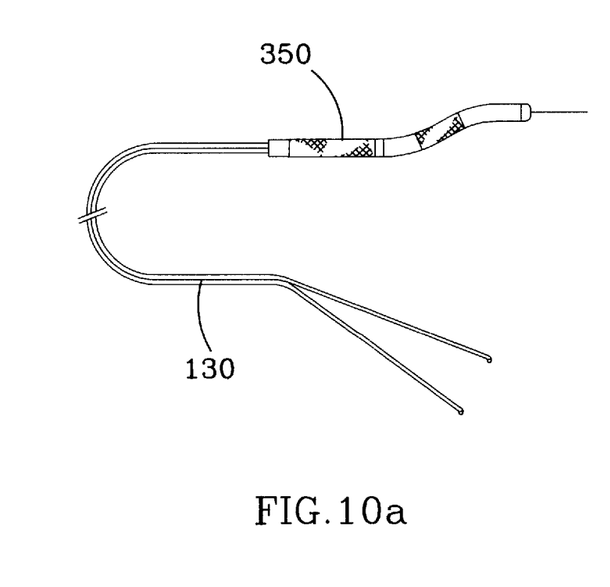
FIGS. 10(a) and 10(b) illustrate different handpiece designs.
Figure 10B:
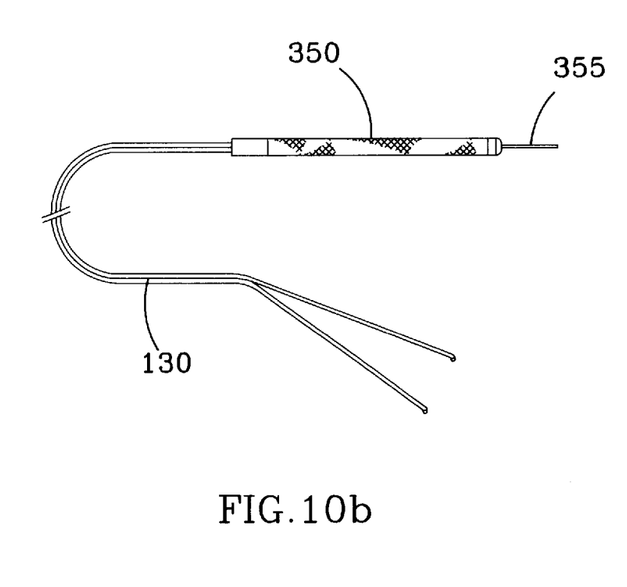
Figure 11A:
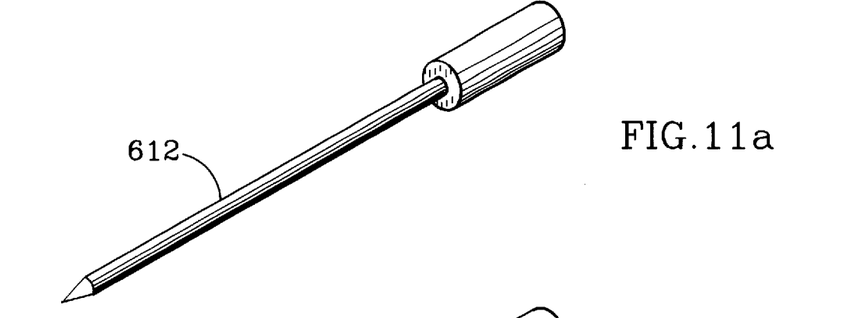
FIGS. 11(a)–11(d) illustrate different configurations of fiber tips 610 of FIGS. 8 and 9(a) in accordance with the present invention.
Figure 11B:
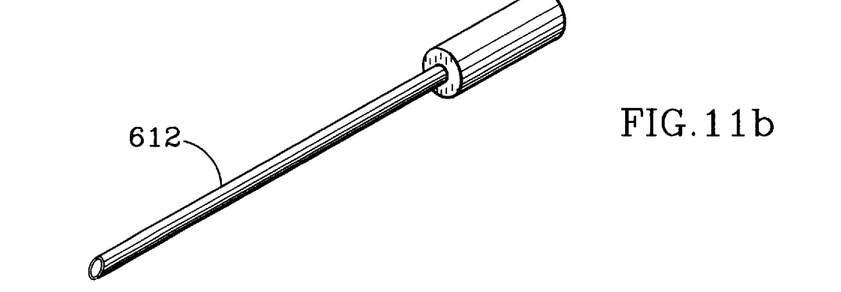
Figure 11C:
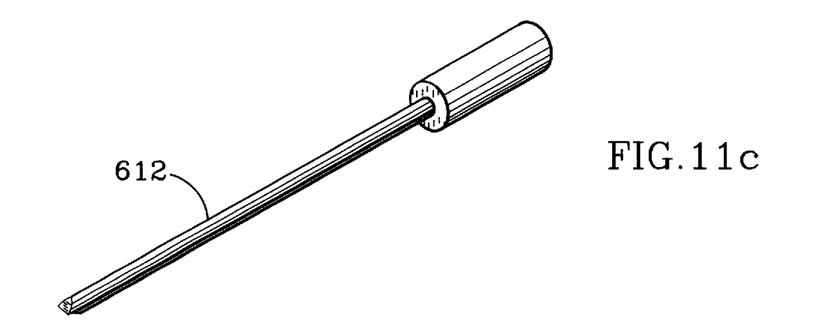
Figure 11D:
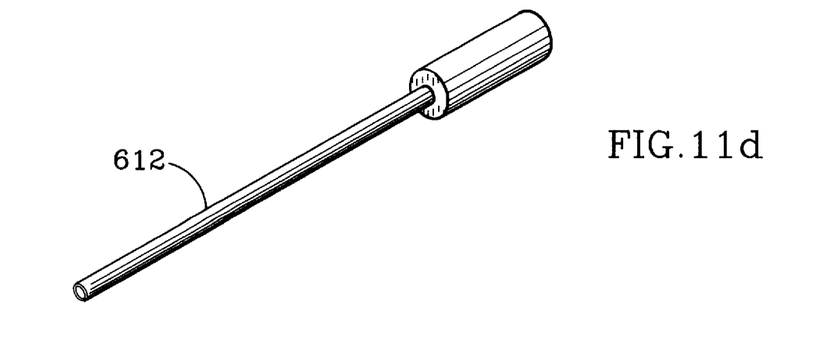

FIGS. 10(a) and 10(b) illustrate different handpiece configurations. In particular, FIG. 10(a) illustrates handpiece 350 having a contra-angle configuration and FIG. 10(b) shows handpiece 350 with extension sleeve 355 for the laser-assisted uvulapalatoplasty (LAUP) medical operation. Preferably, fiber 610 extends through sleeve 355 to expose a deep hard to reach target.

Preferably, fiber 610 and ferrule 4 are formed as a disposable tip 612 detachable from the handpiece 350 to allow for cleaning of the fiber interface with a dry gas purge (air, nitrogen, or argon gas) to remove all water content from the fiber interfaces in the gap between fibers 110 and 610, thereby preventing thermal destruction and light attenuation at the fiber interfaces. Moreover, impurities in the water can absorb light in the 2–19 micron spectral range, and it is therefore important that they be removed as well in order to insure optimum operation.

Preferably, fiber 610 of tip 612 is made from single crystal sapphire. Accordingly, fiber 610 can be easily replaced if damaged or contaminated by easily removing tip 612 from handpiece 350. Further, tip 612 can be removed prior to autoclaving or sterilizing the handpiece, thereby preventing damage to fiber 610. Any fiber other than sapphire that can transmit these mid infrared wavelengths (2.2–19 microns spectra) can not be autoclaved because they are usually hygroscopic and/or heat sensitive. FIGS. 11(a)–11(d) show four geometries of tip 612: cone, 1-sided chisel, 2-sided chisel, and blunt, respectively. Other geometries are also contemplated such as ball ends and triads. The length of the fiber 610 is preferably 10–30 mm, for example, 15 mm, while its diameter is 200 $\mu$m–1 mm, but preferably 600 $\mu$m–1 mm, as noted above.

The combination of two fibers (110 and 610) is advantageous because it obviates the need to replace fiber 110 whenever the output end or tip becomes contaminated or damaged. As noted above, the user simply replaces the disposable fiber 610 instead.

It will be apparent to those skilled in the art that various modifications and variations can be made in the fiber-optic delivery system of the present invention and in construction of this hand held laser device without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An optical device comprising:
   a waveguide; and
   a sheathing substantially surrounding and coupled to said waveguide and exerting an expansive tensile strain on said waveguide when said waveguide and sheathing member are in a straight line configuration, and a progressive less expansive strain on said waveguide as said waveguide and sheathing member are progressively bent.

2. An optical device in accordance with claim 1, further comprising a first fitting fixing said waveguide to said sheathing member at a waveguide first end portion, and a second fitting fixing said waveguide to said sheathing member at a waveguide second end portion.

3. An optical device in accordance with claim 2, wherein said optical device further comprising:
   a housing including a recess rotatably receiving said first fitting, such that angular motion does not induce torsional strain in the optical fiber.

4. An optical device in accordance with claim 3, comprising a bearing positioned between said first fitting and said housing.

5. An optical device in accordance with claim 3, further comprising:
   a source of electromagnetic radiation having an output port;
   a coupling included in said output port for rotatably receiving said second fitting to couple said second end portion of said waveguide to said source of electromagnetic radiation.

6. An optical device in accordance with claim 2, wherein said waveguide is a first optical fiber, said optical device further comprising:
   a housing receiving said first fitting,
   a second optical fiber detachably received in said housing, said second optical fiber is spaced from said first optical fiber within said housing by a distance sufficient to facilitate substantially lossless transmission of electromagnetic radiation from said first optical fiber to said second optical fiber.

7. An optical device in accordance with claim 2, wherein said first and second fittings include first and second ferrules, respectively.

8. An optical device in accordance with claim 7, wherein said first and second ferrules each include a recess for respectively fixedly receiving opposite ends of said sheathing member.

9. The optical device of claim 1, wherein said sheathing member when decoupled from said waveguide has a length which exceeds the length of said waveguide.

10. An optical device in accordance with claim 9, wherein said waveguide is an optical fiber, and the length of said sheathing when decoupled from said fiber exceeds the waveguide length by an amount $\epsilon(\Delta L - \delta \iota)$, where $\epsilon$ is dependent upon a compliance of said optical fiber and said sheathing member, $\Delta L$ is a change of length of said sheathing member when said sheathing member is in a configuration other than said straight-line configuration, and $\delta \iota$ is a change of length of said fiber when said fiber is in said configuration other than said straight-line configuration.

11. An optical device in accordance with claim 1, wherein said waveguide comprises an optical fiber including a material selected from a group comprising monocrystalline sapphire, polycrystalline KRS5, germanium oxide glass, fluoride glass, tellurium halide.

12. An optical device in accordance with claim 1, wherein said waveguide comprises a hollow glass fiber.

13. An optical device in accordance with claim 1, wherein said sheathing member comprises polyetheretherketone plastic.

14. An optical device comprising:
   a casing;
   an optical fiber provided within said casing;
   a first ferrule fixing a first end portion of said optical fiber to a first end portion of said casing;
   said casing having a second end portion which extends beyond a second end portion of said optical fiber when the second end portion of said casing and optical fiber are decoupled from each other; and
   a second ferrule fixing said second end portion of said optical fiber to said second end portion of said casing, thereby creating a tensile strain on said optical fiber when said optical fiber and casing are in a straight-line configuration and a changing level of strain on said optical fiber as said optical fiber and casing are bent.

15. An optical device in accordance with claim 14, wherein said optical fiber comprises a material selected from a group comprising monocrystalline sapphire, polycrystalline KRS5, germanium oxide glass, fluoride glass, tellurium halide.

16. An optical device in accordance with claim 14, wherein said optical fiber comprises a hollow glass fiber.

17. An optical device in accordance with 14, wherein said casing member comprises polyetheretherketone plastic.

18. An optical device in accordance with claim 14, wherein said second end portion of said casing extends beyond said second end portion of said optical fiber when decoupled from said optical fiber's second end portion by an amount $\epsilon(\Delta L - \delta \iota)$, where $\epsilon$ is dependent upon a compliance of said optical fiber and said casing, $\Delta L$ is a change of length of said casing when said casing is in a configuration other than said straight-line configuration, and $\delta \iota$ is a change of length of said fiber when said fiber is in said configuration other than said straight-line configuration.

19. An optical device for directing electromagnetic radiation generated by a source to a target, said optical device comprising:
    a first waveguide having a first end portion and a second end portion coupled to said source of electromagnetic radiation;
    a housing including a recess rotatably receiving said first waveguide such that angular motion of said first waveguide does not induce torsional strain on said first waveguide;
    a second waveguide having first and second portions, said first portion of said second waveguide provided in said housing and spaced from said first end portion of said first waveguide by a distance sufficient to permit substantially lossless transmission of said electromagnetic radiation from said first waveguide to said second waveguide, said second portion of said second waveguide having a termination from which electromagnetic radiation is emitted to impact the target.

20. An optical device in accordance with claim 19, wherein said first and second waveguides include an optical fiber.

21. An optical device in accordance with claim 20, wherein said optical fiber termination of said second waveguide is a cone-shaped tip portion.

22. An optical device in accordance with claim 20, wherein said optical fiber termination of said second waveguide is a chisel-shaped tip portion.

23. An optical device in accordance with claim 20, wherein said optical fiber termination of said second waveguide is a blunt-shaped cylindrical-shaped tip portion.

24. An optical device in accordance with claim 19, wherein said source includes an output port, said optical device further comprising:
    a coupling included in said output port for rotatably receiving said second end portion of said waveguide to couple said second end portion of said waveguide to said source of electromagnetic radiation.

25. An optical device in accordance with claim 19, wherein said source is a laser.

26. An optical device for supplying electromagnetic radiation generated by a source to a target, said optical device comprising:
    an optical fiber having a first end portion and a second end portion coupled to said source of electromagnetic radiation;
    a mounting member fixed to said first end portion of said optical fiber;
    a rotatable member coupled to said mounting member limiting a torque force exerted on said optical fiber; and
    a housing receiving said rotatable member, said housing positioning said optical fiber to output said electromagnetic radiation to said target.

27. An optical device in accordance with claim 26, wherein said rotatable member is a first rotatable member, said optical device further comprising:
    a second rotatable member coupled to said second end portion of said optical fiber, whereby said first and second rotatable members cooperate to limit a torque force on said waveguide.

28. An optical device in accordance with claim 26, wherein said housing is a handpiece for directing said electromagnetic radiation to said target.

29. An optical device in accordance with claim 26, wherein said source of electromagnetic radiation includes a laser.

30. An optical device for delivering electromagnetic radiation generated by a source to a target, said optical device comprising:
    a first optical fiber having a first end portion and a second end portion coupled to said source of electromagnetic radiation;
    a second optical fiber having a first end portion and a second end portion for supplying said electromagnetic radiation to said target; and
    a coupling member receiving said first end portions of said first and second optical fibers, said first end portions of said first and second optical fibers being spaced from each other within said coupling member by a distance sufficient to permit substantially lossless transmission of said electromagnetic radiation from said first optical fiber to said second optical fiber;
    said first optical fiber being tensilely strained when in a straight line configuration and a progressively changing level of strain as it is progressively bent away from straight line.

31. An optical device in accordance with claim 30, wherein said optical fiber of said second waveguide includes a cone-shaped tip portion.

32. An optical device in accordance with claim 30, wherein said optical fiber of said second waveguide includes a chisel-shaped tip portion.

33. An optical device in accordance with claim 30, wherein said optical fiber of said second waveguide includes a cylindrical-shaped tip portion.

34. An optical device in accordance with claim 30, wherein said second optical fiber is disposable.

35. An optical device in accordance with claim 30, wherein said housing is a handpiece housing.

36. An optical device in accordance with claim 30, wherein said first fiber has a first axis and said second fiber has a second axis, said first and second axes being coaligned.

37. An optical device in accordance with claim 30, wherein said first and second fibers are concentrically aligned.

38. A disposable optical fiber for supplying electromagnetic radiation to a biological target, said disposable optical fiber including a first end portion and a second end portion having a chisel-shaped tip.

39. A disposable optical fiber for supplying electromagnetic radiation to a biological target, said disposable optical fiber including a first end portion and a second end portion having a cone-shaped tip.

40. A method for manufacturing an optical cable including an optical fiber and a casing, said method comprising the steps of:

inserting said optical fiber into said casing;

fixing a first end portion of said optical fiber to a first end portion of said casing;

bending said optical fiber and said casing;

fixing a second end portion of said optical fiber to a second end portion of said casing; and straightening said optical fiber and said casing to impose a bias tensile strain on said optical fiber when said optical fiber and said casing are in a straight-line configuration.

41. A method in accordance with claim 40, wherein said step of fixing said first end of said optical fiber includes the steps of:

inserting said first end portion of said optical fiber into a ferrule;

inserting said first end portion of said casing into said ferrule; and attaching said first ends of said optical fiber and said casing to said ferrule.

42. A method in accordance with claim 41, wherein said ferrule is a first ferrule, said step of fixing said second end of said optical fiber includes the steps of:

inserting said second end portion of said optical fiber into a second ferrule;

inserting said second end portion of said casing into said second ferrule; and attaching said second ends of said optical fiber and said casing to said second ferrule.

43. A method in accordance with claim 40, wherein said inserting step includes the step of:

extending a portion of said casing beyond said first end portion of said optical fiber by an amount $\epsilon(\Delta L - \delta\iota)$, where $\epsilon$ is dependent upon a compliance of said optical fiber and said casing, $\Delta L$ is a change of length of said casing when said casing is in a configuration other than said straight-line configuration, and $\delta l$ is a change of length of said fiber when said fiber is in said configuration other than said straight-line configuration.

44. A method in accordance with claim 40, wherein during said bending step said optical fiber and said casing are bent 40%–60% of a minimum bend radius of said optical fiber.

45. An optical device comprising:

a waveguide;

a sheathing substantially surrounding said waveguide; and a restraining member coupling said sheathing to said waveguide to prevent axial compressive failure in said waveguide during bending.

* * * * *